United States Patent [19]

Inwood et al.

[11] Patent Number: 4,469,905

[45] Date of Patent: Sep. 4, 1984

[54] PROCESS FOR PRODUCING AND EXTRACTING $C_2$ TO $C_6$ ALCOHOLS

[75] Inventors: Texas V. Inwood, La Habra; Carlyle G. Wight, Fullerton; Jeffery W. Koepke, La Habra, all of Calif.

[73] Assignee: Union Oil Company of California, Los Angeles, Calif.

[21] Appl. No.: 318,217

[22] Filed: Nov. 4, 1981

[51] Int. Cl.³ .............. C07C 29/04; C07C 29/86; C07C 35/08; C07C 31/10

[52] U.S. Cl. .................. 568/899; 568/835; 568/898; 568/918

[58] Field of Search .......... 568/899, 918, 898, 835

[56] References Cited

U.S. PATENT DOCUMENTS

| | | |
|---|---|---|
| 2,081,721 | 5/1937 | Van Dijck et al. ............ 568/918 |
| 3,455,664 | 7/1969 | Rosscup et al. . |
| 3,548,013 | 12/1970 | Rosscup et al. . |
| 3,793,379 | 2/1974 | Rosscup et al. . |
| 3,955,939 | 5/1976 | Sommer et al. . |
| 3,988,381 | 10/1976 | Dulog . |
| 3,994,983 | 11/1976 | Webers et al. . |
| 4,067,902 | 1/1978 | Werges . |
| 4,182,920 | 1/1980 | Giles et al. ............ 568/898 |

FOREIGN PATENT DOCUMENTS

| | | |
|---|---|---|
| 1208144 | 10/1970 | United Kingdom . |
| 1381455 | 1/1975 | United Kingdom . |
| 1386195 | 3/1975 | United Kingdom . |
| 1390164 | 4/1975 | United Kingdom . |
| 1396488 | 6/1975 | United Kingdom . |

OTHER PUBLICATIONS

Vener, "Chemical Engineering", Jul. 1955, pp. 204, 205.

Primary Examiner—J. E. Evans
Attorney, Agent, or Firm—Dean Sandford; Gregory F. Wirzbicki; Cleveland R. Williams

[57] ABSTRACT

A process for producing and recovering a $C_2$ to $C_6$ alcohol, which comprises contacting water and a $C_2$ to $C_6$ olefin with a hydration catalyst comprising an acidic ion exchange resin in a reaction zone under reaction conditions, said reaction zone containing multiple water quench points and multiple olefin injection points, and counter-currently contacting the reaction product with a solvent to extract the $C_2$ to $C_6$ alcohols therefrom.

23 Claims, 3 Drawing Figures

PROCESS FOR PRODUCING AND EXTRACTING C₂ TO C₆ ALCOHOLS

BACKGROUND OF THE INVENTION

1. Field of the Invention

This invention relates to a process for the production of $C_2$ to $C_6$ alcohols, particularly isopropanol, by the hydration of $C_2$ to $C_6$ olefins, for example, propylene, in the presence of an acidic ion exchange resin as a hydration catalyst, and for the recovery of $C_2$ to $C_6$ alcohols from the reaction product.

2. Description of the Prior Art

Isopropanol was the first petrochemical made in the United States and has been commercially available since 1920. Previously, isopropanol was produced by the indirect hydration of propylene. This was accomplished by esterification of propylene with sulfuric acid and the subsequent hydrolysis of the ester to the alcohol and sulfuric acid. This process, however, requires reconcentration of the sulfuric acid, leads to corrosion of apparatus, high heat requirements and pollution, all of which dictate the need for development of direct hydration routes to produce alcohols from olefins.

More recently, three processes have been developed to catalytically hydrate olefins to alcohols, namely, gas phase hydration of olefins using a fixed-bed catalyst consisting of a supported phosphoric acid, coexisting gas-liquid phase hydration of olefins in the presence of a cation-exchange resin, and liquid-phase hydration of an olefin in the presence of a dissolved tungsten catalyst.

It has been demonstrated that alcohol formation, in an olefin hydration reaction, is generally favored by low temperatures and high pressures, since the reaction equilibrium of olefin to alcohol is satisfactory at these conditions. Thus, a mechanism to control the reaction temperature of an olefin hydration reaction is highly beneficial in a process for producing alcohols.

The hydration of olefins to alcohols in the presence of a catalyst is known and appreciated by the prior art. For example, U.S. Pat. No. 3,994,983, issued Nov. 30, 1976, relates to a process for the production of $C_2$ to $C_6$ alcohols by hydration of olefins in the presence of water and an acidic cation exchange resin catalyst. In particular, vaporous lower aliphatic olefins containing from 2 to 6 carbon atoms are contacted with water in the liquid phase in the presence of acids or strongly acidic solids at elevated temperature and pressure.

U.S. Pat. No. 3,955,939 issued May 11, 1976 discloses a process for recovering a water-free mixture of isopropyl alcohol, diisopropyl ether, and by products consisting of n-propanol, acetone, hexanol, etc. from the catalytic hydration of propylene in the gaseous phase. The product from the hydration reaction is separated from water utilizing diisopropyl ether produced in the process. The water-free mixture thus formed is used as an additive for gasoline.

Another process for producing isopropanol and blending the same with gasoline is disclosed in U.S. Pat. No. 3,455,664 issued July 15, 1969. Propylene is hydrated with water to isopropyl alcohol at increased temperature and pressure in the presence of a catalyst consisting, for example, of a polystyrene divinyl benzene sulfonic acid resin. Other suitable catalysts include silica-alumina, acidic clays, reduced tungsten oxides, etc. The isopropyl alcohol thus produced is extracted with a gasoline reformate and blended with gasoline.

U.S. Pat. No. 3,988,381, issued Oct. 26, 1976 discloses a hydration method and catalyst for producing isopropanol. The catalyst is a crosslinked copolymer produced by polymerizing diethylvinyl-phosphonate and divinylsulfone in the presence of a radical initiator, i.e., azoisobutyronitrile under a nitrogen atmosphere. Isopropanol is produced by hydrating propylene with water in contact with the above crosslinked copolymer.

U.S. Pat. No. 3,548,013, issued Dec. 15, 1970 discloses a process for the production of $C_3$ to $C_6$ alcohols from the corresponding olefins, wherein a $C_3$ to $C_6$ olefins is hydrated to an alcohol with water in the presence of a hydration catalyst, for example, a polystyrene divinyl benzene sulfonic acid resin. The alcohol produced in the process is separated from the reaction mixture by flash distillation.

As can readily be determined from the above, there is an ongoing research effort to provide new and improved methods for producing alcohols from olefins using indirect as well as direct hydration catalysts.

Accordingly, it is an object of this invention to provide a process for the direct hydration of $C_2$ to $C_6$ olefins to alcohols.

Another object of this invention is to provide a hydration process for producing an alcohol wherein said alcohol is counter currently extracted with a solvent to provide an economical method of separating the alcohol from water in the process.

These and other objects of the invention will be apparent to those skilled in the art from the following description in conjunction with the drawings.

SUMMARY OF THE INVENTION

The present invention relates to a process for producing and extracting a $C_2$ to $C_6$ alcohol which comprises contacting water and a $C_2$ to $C_6$ olefin with a hydration catalyst comprising an acidic ion exchange resin in a reaction zone under hydration conditions, and thereafter extracting said $C_2$ to $C_6$ alcohol with a solvent. The reaction zone preferably contains multiple water quench points and olefin injection points, in addition, a drying step after extracting the alcohol with a solvent helps to separate the alcohol from water and other reaction products, including unreacted olefin.

BRIEF DESCRIPTION OF THE DRAWINGS

The invention is further described by reference to the appended drawings, wherein.

DETAILED DESCRIPTION OF THE INVENTION

This invention resides in a process for producing and recovering a $C_2$ to $C_6$ alcohol by contacting a feed stream comprising water and a $C_2$ to $C_6$ olefin and optionally a $C_2$ to $C_6$ paraffin under hydration conditions with a hydration catalyst comprising an acidic ion exchange resin in a reaction zone which will be described in greater detail hereinafter, and thereafter extracting the alcohol thus produced with a solvent selected from gasoline reformate, isopropyl ether and benzene and mixtures thereof. The reaction zone may contain multiple water quench points and multiple olefin injection points to help control the reaction temperature and ensure a high conversion rate of olefin and high yield of the desired alcohol.

The process of the invention will now be explained with reference to the accompanying drawings.

Figure 1:
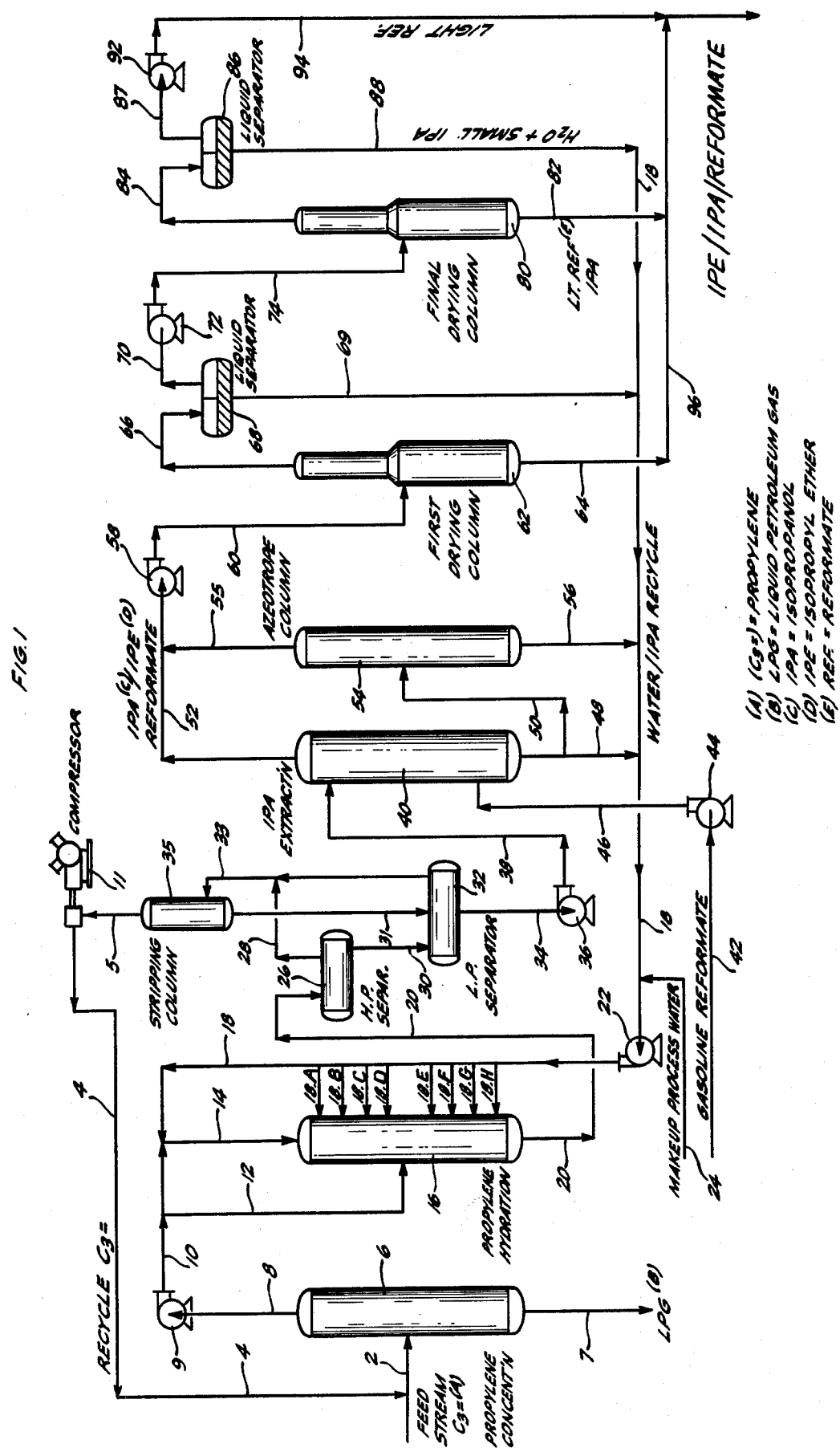
FIG. 1 is a schematic flow diagram incorporating suitable apparatus for carrying out the hydration process of this invention using gasoline reformate as the extracting solvent.

FIG. 1 illustrates a preferred embodiment of the hydration process herein. Particularly, a feed stream comprising a $C_2$ to $C_6$ olefin charged via conduit 2 with recycle olefin from conduit 4 to olefin concentration vessel 6 from which liquid petroleum gas (paraffin) is discharged via conduit 7 to conventional collection apparatus. Optionally, the feed stream may contain from about 0 mole percent to about 50 mole percent, especially from about 1 mole percent to about 35 mole percent of a $C_2$ to $C_6$ paraffin in addition to the olefin. Concentration vessel 6 is a pressure vessel, equipped with a reboiler heater at the bottom and a reflux condensor at the top, (neither of which are shown) which operate at conventional conditions.

Olefins suitable for use herein from 2 to 6 carbon atoms and are selected from the group consisting of ethylene, propylene, butene, pentene, hexene or cyclohexene, or a mixture thereof. The preferred olefin is propylene. Normally, impurities such as $C_2$ to $C_6$ paraffins may be included in the feed stream with the water and olefin without deleterious effect upon the hydration reaction. Paraffins which may be included in the feed stream with water and the olefin include ethane, propane, butane, pentane, hexane, etc. and mixtures thereof.

Olefin and a small amount of entrained paraffin, when a paraffin is present in the feed stream, are transported from vessel 6 through conduit 8, pump 9 and conduits 10, 12 and 14 to hydration reaction zone 16 which comprises either a single hydration reactor or two or more hydration reactors, for example 2 to 10 hydration reactors connected in series. Alternatively, the reaction zone may comprise a single hydration reactor containing two or more catalyst beds connected in series. In a preferred mode, the hydration reaction zone contains two pressure reactors connected in series.

Multiple water quench points and multiple olefin injection points in the hydration process described herein serve a two-fold purpose. Namely, the reaction temperature is controlled in the desired temperature range and additional olefin is added at strategic locations within the reaction zone to ensure a high conversion rate of olefin and high yield of the desired alcohol. In a preferred mode, from about 1 to about 10 multiple water quench points and from about 1 to about 10 multiple olefin injection points are sufficient for the process herein. It should be noted, however, that up to 30 water quench points and up to 30 olefin injection points may be used, for example, in a commercial process.

Recycle water which may contain isopropanol and a small amount of ether produced in the hydration reaction, together with makeup water from conduit 24, is transported through conduit 18, pump 22, lines 18(a) to 18(h), and conduit 14 into hydration reaction zone 16 which contains an ion exchange type hydration catalyst, for example, an acidic ion exchange resin comprising a sulfonated styrene divinylbenzene copolymer. These type catalysts possess a unique porous structure referred to as a macroreticular structure which has a high degree of true porosity wherein the pores are rigid and fixed within the resin structure. This high porosity gives rise to a large surface area which is conducive to high catalytic activity. In addition, the macroreticular structure of the catalysts herein permits ready access of liquid or gaseous reactants to the hydrogen ions present throughout the resin. This accessibility of non-aqueous solutions to hydrogen ions is not found in conventional ion exchange resins. In addition these resins are completely insoluble in strong acids, such as hydrochloric acid and sulfuric acid, concentrated alkali, aliphatic and aromatic hydrocarbons, water, alcohols, ethers, and most other common solvents.

Hydration catalysts which are suitable for use herein are sulfonated styrene divinylbenzene copolymers produced in the form of round beads and marketed by the ROHM and Haas Company under the tradenames of Amberlite 252H+, Amberlyst 15H+ and Amberlyst XN-1010H+. These catalysts are strongly acidic cation exchange resins. It should be noted that the above catalysts are available in either the sodium form or the hydrogen form. Although it is not desired to be bound by an theory, it is known that the sodium form of the catalyst does not catalyze the hydration reaction herein. The exact reaction mechanism is unknown, however, it is believed that the carbonium ion form of the olefin is not formed when the catalyst is in the sodium exchange form. The carbonium ion intermediate is believed necessary to convert an olefin to an alcohol.

Water, olefin and incidentally included paraffin are reacted in contact with a sulfonated styrene divinylbenzene copolymer in reaction zone 16 at temperatures which are sufficiently high to initiate a reaction between water and the particular olefin used to prepare the corresponding alcohol. Generally, temperatures suitable for use in this process are from about 200° F. to about 350° F., especially from about 255° F. to about 300° F. Preferably, the water and olefin are reacted at a mole ratio of water to olefin of from about 5:1 to 50:1, especially from about 10:1 to about 25:1.

Similarly, pressures which are suitable for use in the hydration reaction zone preferably are above 1,000 p.s.i.g., but should not be in excess of about 5,000 p.s.i.g., an especially desirable pressure range is from about 1,200 p.s.i.g., to about 1,500 p.s.i.g. Normally, the hydration reaction herein is conducted at a weight hourly space velocity (WHSV) of from about 0.1 to about 10.0, preferably from about 0.5 to about 4.0 pounds of water, olefin and incidentally included paraffin per pound of catalyst per hour.

Generally, the styrene divinylbenzene copolymer catalysts herein will convert at least 50 percent generally from 70 to 90 percent of the olefin to the corresponding alcohol. The reaction product thus produced consists of the desired alcohol, water, the corresponding ether, unreacted olefin and paraffin, when a paraffin is introduced into the feed stream. The alcohol produced in the hydration reaction will, of course, depend upon the olefin introduced into the feed stream. Desirable alcohols will have from 2 to 6 carbon atoms and include ethanol, isopropanol, butanol, pentanol, hexanol, etc. The preferred alcohol is isopropanol.

Ethers produced as a by-product of the hydration reaction herein have from $C_4$ to $C_{12}$ carbon atoms, for example, ethyl ether, isopropyl ether, butyl ether, amyl ether, hexyl ether, etc. The ether produced will depend upon the olefin introduced into the process.

The reaction product is next transported through conduit 20 to high pressure separator 26 where liquids in the reaction product are separated from gases. The pressure in the high pressure separator is substantially the same as the hydration reaction pressure. Liquid reaction product is transported via conduit 30 to low pressure separator 32 where in route the pressure is reduced to atmospheric pressure. The vapor phase in separator 32 comprising water, unreacted olefin, a small amount of alcohol, ether and paraffin, when a paraffin is included in the feed stream, is transported through conduit 33 to stripping column 35. The overhead from high pressure separator 26 is additionally transported through conduits 28 and 33 to stripping column 35. Unreacted olefin, a small amount of entrained alcohol and ether, and a paraffin when a paraffin is present in the feed stream, are recycled through conduit 5, compressor 11 and conduits 4 and 2 to concentration vessel 6. The bottoms from stripping column 35 consisting of reaction product containing a small amount of water is transported through conduit 31 to low pressure separator 32. The liquid phase reaction product is transported from low pressure separator 32 through conduit 34, pump 36 and conduit 38 to the top of extraction column 40.

A solvent comprising gasoline reformate is introduced through conduit 42, pump 44 and conduit 46 to the bottom of extraction column 40 where alcohol, for example isopropanol, and ether, for example isopropyl ether, are counter-currently extracted from the water phase which is withdrawn from the bottom of extraction column 40. Any conventional extraction column may be used in this process; however, the preferred column is a Karr column marketed commercially by the Chem-Pro Equipment Corporation. The Karr column is preferably equipped with a series of connected perforated plates having agitation means for providing reciprocating motion to ensure complete mixing of the reaction product and solvent. Generally, the reaction product and solvent are mixed in a volume ratio of from about 2:1 to about 1:5, especially from about 1:1 to about 1:3. It should be noted that benzene and isopropyl ether may be used as the solvent herein, in addition to the gasoline reformate; however, the preferred solvent in the process described in FIG. 1 is gasoline reformate.

The top phase or overhead in extraction column 40 comprising a small amount of water and a major portion of alcohol, ether, and solvent, for example gasoline reformate, is transported through conduit 52, pump 58 and conduit 60 to first drying column 62. The drying column may be either a single column or two or more columns connected in series. The bottom phase of extraction column 40 comprising a large amount of water and a small amount of alcohol and ether is transported through conduit 48 and 50 to azeotrope column 54 and through conduits 48, and 18, together with makeup process water from conduit 24, through pump 22, conduits 18(a) to 18(h), and 14 to hydration reaction zone 16.

In azeotrope column 54, an azeotrope of water and alcohol is produced overhead and combined with the reformate phase withdrawn from the top of extraction column 40 and transported through conduit 52, pump 58 and conduit 60 to drying column 62. A large amount of water containing a small amount of alcohol is produced from the bottom of azeotrope column 54, mixed with the water phase withdrawn from the bottom of extraction column 40 and recycled to hydration reaction zone 16 through conduits 56, 18, pump 22, and conduits 18(a) to 18(h) and 14.

Drying column 62 is a standard drying column which separates water from alcohol, ether and solvent by distillation. It should be noted that most of the water is removed from the reaction product prior to introduction of the reaction product into the drying column, i.e. by separation in extraction column 40 and azeotrope column 54, thus reducing the overall energy and cost requirements of the process.

The dried reaction product is transported from first drying column 62 through conduits 64 and 96 to storage facilities. The overhead from drying column 62 comprising water containing alcohol, ether and solvent, is transported through conduit 66 to liquid separator 68, which comprises a standard weir type apparatus which separates a hydrocarbon rich top phase from a bottom phase comprising water and alcohol with a small amount of entrained hydrocarbons. The bottom phase is combined with the water phases from extraction column 40 and azeotrope column 54 and transported through conduits 69, 18, pump 22, etc. to hydration reaction zone 16. The top organic rich phase comprising a small amount of water, alcohol, ether and solvent is transported through conduit 70, pump 72, and conduit 74 to final drying column 80, where the bottoms product comprising alcohol, ether, and solvent are transported through conduits 82 and 96 to storage facilities.

The overhead from drying column 80 is transported through conduit 84 to a second liquid separator 86 where a top organic rich phase comprising alcohol, ether and solvent is transported via conduit 87, pump 92 and conduit 94 to storage facilities. The bottom phase from liquid separator 86 comprising water with entrained alcohol, ether and solvent is combined with the other water phase and recycled to hydration reaction zone 16 via conduits 88, 18, pump 22, etc.

Figure 2:
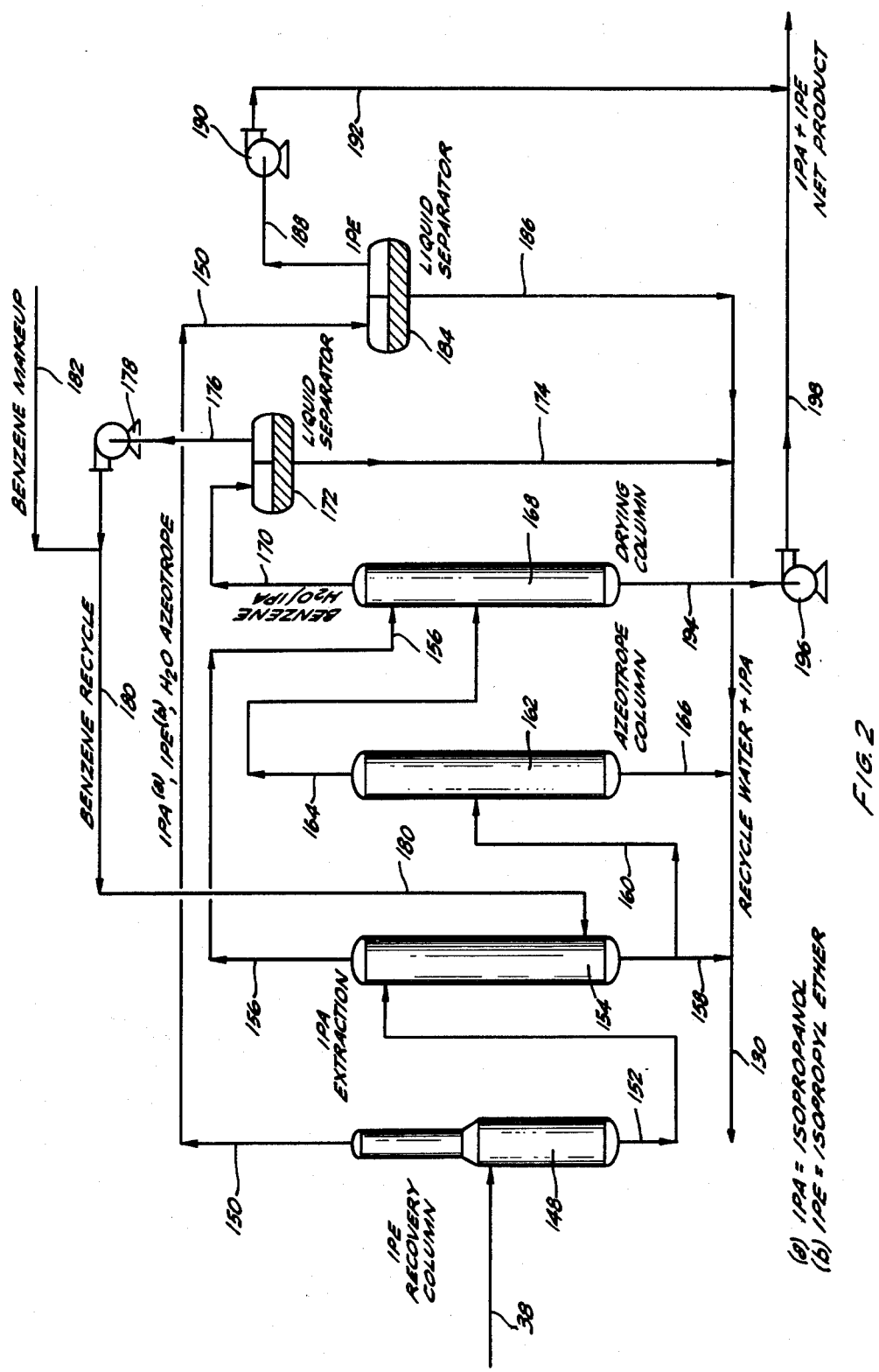
FIG. 2 is a schematic flow diagram illustrating an alternate hydration process for producing $C_2$ to $C_4$ alcohols using benzene as the extracting solvent.

FIG. 2 illustrates an optional embodiment of the hydration process herein which uses benzene as the extraction solvent. The process illustrated in the schematic flow diagram for FIG. 2 is substantially the same as the flow diagram for FIG. 1 with the following exceptions:

The liquid phase reaction product from the low pressure separator 32, for example, as depicted in FIG. 1, is transported through conduit 38 to ether stripping column 148, where the top phase or overhead comprising a large amount of ether, for example, isopropyl ether and a small amount of alcohol, for example, isopropanol and water is transported through conduit 150 to liquid separator 184. Isopropyl ether in liquid separator 184 is recovered via conduit 188, pump 190, conduit 192, admixed with isopropanol and isopropyl ether from conduit 198 and transported to storage facilities.

The bottom phase from stripping column 148 comprising isopropanol, water and a negligible amount of entrained isopropyl ether, is transported via conduit 152 to the top of extraction column 154. A solvent comprising benzene is transported via conduit 182, admixed with recycle benzene and isopropanol and transported through conduit 180 to the bottom of extraction column 154, where the bottoms comprising water and a small amount of isopropanol, isopropyl ether and entrained benzene, is transported through conduits 158 and 160 to azeotrope column 62. A portion of the bottoms from extraction column 154 is additionally transported through conduit 158, admixed with recycle water and isopropanol in conduit 130, and recycled to the hydration reactor, for example, as depicted in FIG. 1.

In azeotrope column 162, an azeotrope of water and isopropanol is produced overhead and transported to drying column 168 via conduit 164. A large amount of water containing a small amount of isopropanol and entrained benzene is produced from the bottom of azeotrope column 162, mixed with the water phase withdrawn from the bottom of liquid separators 172 and 184 and recycled to hydration reactor 16, for example, as depicted in FIG. 1.

The top phase or overhead in extraction column 154 comprising a small amount of water and a major portion of isopropanol and benzene, is transported through conduit 156 to drying column 168, a standard drying column which separates water from isopropanol and benzene by distillation.

The dried product from drying column 168 comprising isopropanol is transported via conduit 194, pump 196 and conduit 198 to storage facilities. The overhead from drying column 168 comprising isopropanol, isopropyl ether and benzene is transported via conduit 170 to liquid separator 172, which comprises a standard weir, type apparatus which separates benzene and isopropanol from water containing a small amount of isopropanol. Benzene and isopropanol are recycled through conduit 176, pump 178 and conduit 180, admixed with makeup benzene from conduit 182 and transported to extraction column 154. A large amount of water containing a small amount of isopropanol and entrained benzene is produced from the bottom of liquid separator 172, transported through conduits 174 and 130 to hydration reactor 16, for example, as depicted in FIG. 1.

Figure 3:
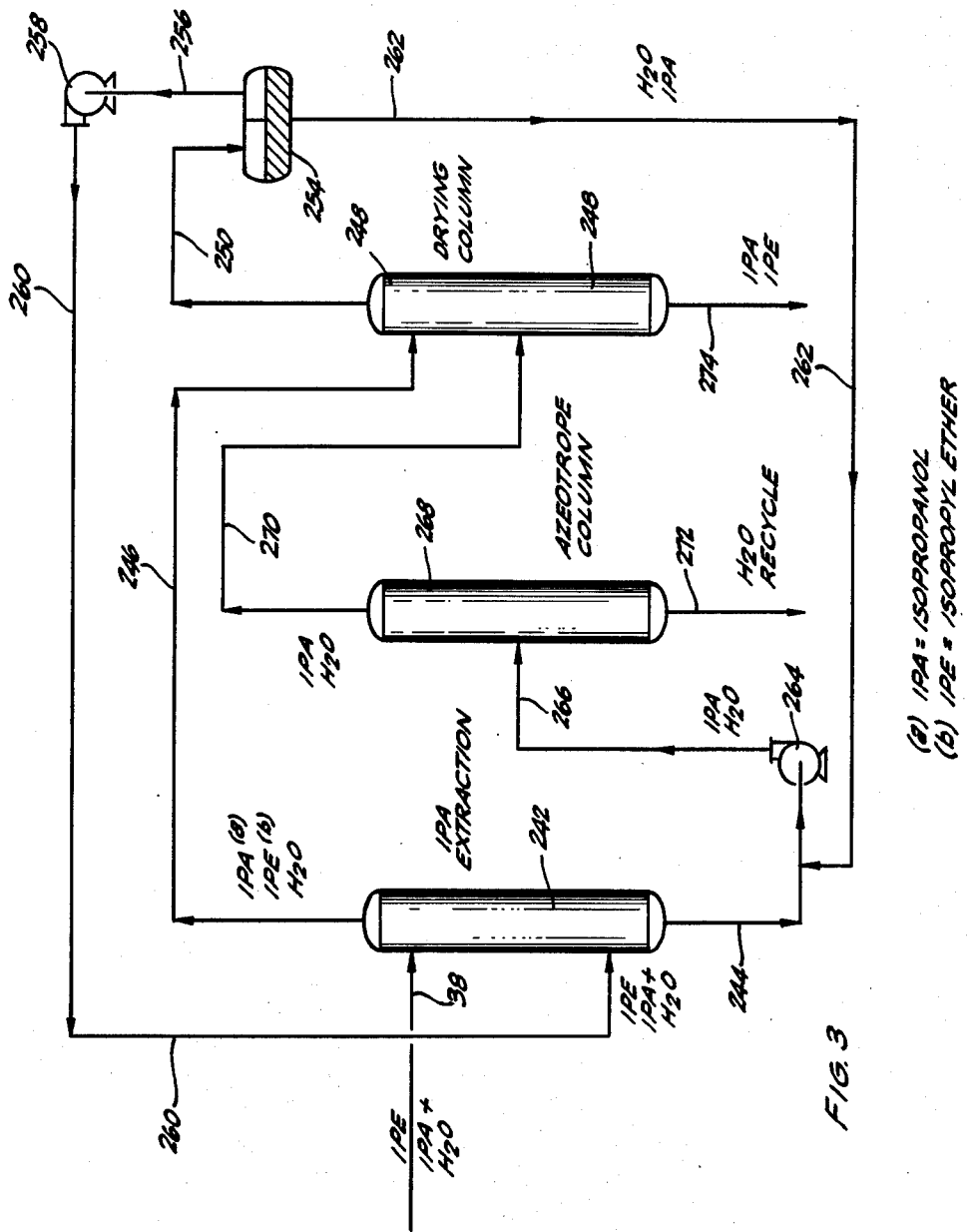
FIG. 3 is yet another schematic flow diagram illustrating suitable apparatus for carrying out the hydration process herein using isopropyl ether as the extracting solvent.

FIG. 3 illustrates yet another optional embodiment of the present process using ether generated in the process as the extracting solvent. The preferred ether is isopropyl ether. The process illustrated in FIG. 3 is substantially the same as the process illustrated in FIG. 1 with the following exceptions:

The liquid phase reaction product comprising water, alcohol, for example, isopropanol, and ether for example, isopropyl ether from low pressure separator 32, for example, as depicted in FIG. 1, is transported through conduit 38 to the top of extraction column 242. A solvent comprising isopropyl ether and containing a small amount of isopropanol and water is transported via conduit 260 to the bottom of extraction column 242 where isopropanol is countercurrently extracted by the isopropyl ether.

The top phase or overhead, produced in extraction column 242, comprising isopropanol, isopropyl ether and a small amount of water is transported through conduit 246 to drying column 248 which comprises a standard drying column which separates water from isopropanol and isopropyl ether by distillation.

The bottom phase from extraction column 242 comprising a large amount of water and a small amount of isopropanol and entrained isopropyl ether is transported to azeotrope column 268 via conduit 244, admixed with water, isopropanol and entrained isopropyl ether from liquid separator 254, through pump 264 and conduit 266.

In azeotrope column 268, a large amount of water is recycled through conduit 272 to hydration reactor 16, for example, as depicted in FIG. 1. A top phase or azeotrope of water isopropanol and isopropyl ether produced in column 268, is transported via conduit 270 to drying column 248 where together with water, isopropanol and isopropyl ether from line 246, isopropanol and isopropyl ether are produced as column bottoms and transported via conduit 274 to storage facilities.

The top phase from drying column 248 is transported through conduit 250 to liquid separator 254, which is a standard weir type apparatus which produces an overhead comprising a large amount of isopropyl ether, and a small amount of isopropanol and water. The upper phase from liquid separator 254 is transported via conduit 256, pump 258 and conduit 260 to the bottom of extraction column 242.

A large amount of water and a small amount of isopropanol and isopropyl ether are recycled from liquid separator 254 through conduits 262, 244, pump 264 and conduit 266 to azeotrope column 268.

The invention will be further described with reference to the following non-limiting Examples.

EXAMPLE I

Propylene is hydrated with water to produce isopropanol in two hydration reactors connected in series containing 500 ml of wet Amberlite 252H+ resin in each reactor, which is equivalent to 179.5 grams of the resin on a dry basis in each reactor. The support for the resin consists of 3 inches each of 4 to 6 mesh quartz (bottom layer), 6-8 mesh quartz (middle layer), and 10-20 mesh quartz (top layer). The 500 ml of Amberlite 252H+ is placed on top of the quartz support. An additional 1,200 grams of 6 to 8 mesh quartz is placed on top of the resin catalyst as a preheat section which serves as a feed distribution and preheat area.

The two hydration reactors are downflow tubular reactors having a length of 114 inches, an inside diameter of 2.17 inches, equipped with insert tubes having a length of 64 inches and giving a final inside diameter of 1.682 inches. In addition the reactors are equipped with teflon-coated, 0.38 outside diameter, central-longitudinal thermo-wells. The reactor are immersed in heated silicone fluid baths provided with temperature control and agitation means.

De-ionized water and propylene at a mole ratio of 15:1 are introduced into the first reactor (R-1) and contacted with the catalyst at a weight hourly space velocity of 1.4 pounds of water and propylene per pound of catalyst per hour, a pressure of 1,500 p.s.i.g. and a temperature of 276° F.

The reaction product from R-1, including water, isopropanol, isopropyl ether, unreacted propylene and additional propylene, 75 weight percent of the propylene feed to R-1, are introduced into the second reactor (R-2), which is connected to R-1 in series, at a weight hourly space velocity of 1.56 pounds of water, isopropanol, isopropyl ether and propylene per pound of catalyst per hour, a pressure of 1,500 p.s.i.g. and a temperature of 278° F.

The run is conducted over a 32 day period with an average product of 94.95 weight percent isopropanol and 5.05 weight percent isopropyl ether at an overall conversion rate of 85.5 percent of propylene to isopropanol.

Next, the reaction product consisting of isopropanol, isopropyl ether and water, is transported to a counter current and fractional liquid extraction column (Karr column) having an inside diameter of 1 inch, a length of 152 inches and containing 50 perforated plates agitated in reciprocating motion at a speed of 260 strokes per minute. The reaction product from reactors R-1 and R-2 is fed to the top of the extraction column at a rate of 275 grams per hour and a solvent comprising gasoline reformate is fed to the bottom of the extraction column at a rate of 197.1 grams per hour. The organic rich phase extraction product consisting of isopropanol, isopropyl ether, gasoline reformate and some water is dried utilizing a 20-plate, Oldershaw still (perforated tray type), having a length of 25 inches and an outside diameter of 1 inch. The still is equipped with a standard water cooled condenser and thermometer. The distillation is performed at 1 atmosphere of pressure, a temperature of 167° F. and a reflux ratio of 5:1. Substantially all of the water is separated from the extraction product consisting of isopropanol, isopropyl ether and gasoline reformate.

EXAMPLE II

Propylene is hydrated with water to isopropanol in two pressure reactors connected in series, containing 179.5 grams of Amberlite 252H+ on a dry basis in each reactor. A resin support consisting of 3 inches of 4 to 6 mesh quartz (bottom layer), 3 inches of 6 to 8 mesh quartz (middle layer) and 3 inches of 10 to 20 mesh quartz (top layer) is placed in the bottom of the reactor. Amberlite 252H+ (179.5 grams) is placed on top of this quartz support. An additional 1,200 grams (26 inches) of 6 to 8 mesh quartz is placed on top of the Amberlite 252H+ which serves as a feed distribution and preheat area.

The two hydration reactors are downflow tubular reactors connected in series, having a length of 114 inches, an inside diameter of 2.17 inches, equipped with insert tubes having a length of 64 inches and an inside diameter of 1.68 inches. Additionally, each reactor contains a teflon-coated, 0.38 outside diameter, central-longitudinal thermowell. The reactors are immersed in heated silicone baths provided with temperature control and agitation means.

Recycle de-ionized water containing 20.5 weight percent isopropanol and propylene are introduced into the first reactor (R-1) in a water and isopropanol/propylene mole ratio of 21.65:1, and contacted with the catalyst at a pressure of 1,500 p.s.i.g., a temperature of 276° F., and a weight hourly space velocity of 2.24 pounds of water, isopropanol and propylene per pound of catalyst per hour.

The reaction product from R-1, including water, unreacted propylene, isopropanol and isopropyl ether and an additional 70 percent by volume of propylene is introduced into the top of the second reactor (R-2), which is connected in series with R-1, at a weight hourly space velocity of 2.37 pounds of reaction product per pound of catalyst per hour, a pressure of 1,500 p.s.i.g. and a temperature of 284° F.

The run is conducted over a period of 79 days yielding an average product of 80 weight percent isopropanol and 20 weight percent isopropyl ether with an overall conversion rate of propylene to isopropanol of 82 percent.

The reaction product of isopropanol, and isopropyl ether, including water and unreacted propylene, is next, transported to a counter current and fractional liquid extraction column (Karr column) having an inside diameter of 1 inch, a length of 152 inches, containing 50 perforated plates connected by a central shaft, said plates being agitated in reciprocating motion at a speed of 154 strokes per minute. The reaction product from reactors R-1 and R-2 is fed to the top of the extraction column at a rate of 400.4 grams per hour and a solvent comprising benzene is fed to the bottom of the extraction column at a rate of 120.3 grams per hour.

The organic rich layer of the extraction product comprising isopropanol, isopropyl ether, benzene, and water is dried using a 20-plate, Oldershaw still (perforated tray type), having a length of 25 inches and an outside diameter of 1 inch. The still is equipped with a standard water cooled condenser and thermometer. The distillation is performed at 1 atmosphere of pressure, a final overhead temperature of 170° F. and a reflux ratio of 5:1.

EXAMPLE III

Propylene is hydrated to isopropanol using the procedure of Example II with the following exception: isopropyl ether is substituted for the benzene in the counter current and fractional liquid extraction column, with substantially the same results occurring.

EXAMPLE IV

Propylene is hydrated with water to produce isopropanol in two pressure reactors connected in series containing 179.5 grams of Amberlite 252H+ resin on a dry basis in each reactor. A support for the resin consisting of 3 inches each of 4 to 6 mesh quartz (bottom layer), 6 to 8 mesh quartz (middle layer), and 10 to 20 mesh quartz (top layer) is placed in each reactor. The Amberlite 252H+ is placed on top of the quartz support. An additional 1,200 grams of 6 to 8 mesh quartz is placed on top of the resin catalyst which serves as a feed distribution and preheat area.

The two hydration reactors are the same as those described in Example I. A feed stream comprising recycle water, propylene and propane is introduced into the top of the first reactor (R-1) and contacted with the catalyst. The recycle water comprises 82.48 percent de-ionized water, 17.12 percent isopropanol and propane, 0.10 percent of isopropyl ether and 0.30 percent benzene which is the saturation amount of benzene from the extraction step of the process described below. The propylene and propane are present at a ratio of 92 percent propylene to 8 percent propane. The reaction is performed at a pressure of 1,500 p.s.i.g., a temperature of 271° F. and a weight hourly space velocity of 1.55 pounds of feed stream per pound of catalyst per hour.

The reaction product from R-1 and additional propylene, 70 weight percent of the propylene fed to R-1 are introduced into the top of reactor R-2, which is connected in series with R-1, at a weight hourly space velocity of 1.64 pounds of reactor product and propylene per pound of catalyst per hour, a pressure of 1,500 p.s.i.g. and a temperature of 278° F. The reaction product of each reactor includes water, a trace amount of benzene, isopropanol, isopropyl ether, and cumene. The conversion of propylene to isopropanol in each reactor is 70 percent with an overall conversion rate of 82 percent.

Isopropyl ether is recovered using a standard distillation column and the remaining reaction product comprising water and isopropanol from reactor R-2 is transported to a counter current and fractional liquid extraction column (Karr column) having an inside diameter of 1 inch, a length of 152 inches, and containing 50 perforated plates agitated in reciprocating motion at a speed of 250 strokes per minute. The reaction product from reactor R-2 is fed to the top of the extraction column at a rate of 277.3 grams per hour and benzene is fed to the bottom of the extraction column at a rate of 68.79 grams per hour. The organic rich phase of the extraction product containing isopropanol, isopropyl ether, propane, benzene and water is dried utilizing a 20-plate, Oldershaw still (perforated tray type), having a length of 25 inches and an outside diameter of 1 inch. The still is equipped with a standard water cooled condenser and thermometer. The distillation is performed at 1 atmosphere of pressure, a temperature of 173° F. and a reflux ratio of 5:1. The distillation feed stream has the following composition on a weight percent basis: bottoms (31.05), overhead upper phase (64.51), overhead lower phase (4.44). The reaction product separates into three distinct phases as indicated in Table 1 below:

TABLE 1

|  | Isopropanol (Wt. %) | Benzene (Wt. %) | Water (Wt. %) |
| --- | --- | --- | --- |
| Bottoms | 97.65 | 1.60 | 0.75 |
| OHUP$^{(E)}$ | 19.06 | 78.72 | 2.23 |
| OHUP$^{(F)}$ | 20.13 | 0.18 | 79.70 |

$^{(E)}$OHUP = overhead upper phase.
$^{(F)}$OHLP = overhead lower phase.

The bottom phase in Table 1 above, is transported to storage facilities. The two phases of the overhead are separated in a separatory funnel and the lower water rich phase is recycled for use in the hydration reactors. The upper hydrocarbon rich phase is transported to storage facilities.

Obviously, many modifications and variations of the invention, as hereinbefore set forth, may be made without departing from the spirit and scope thereof, and therefore only such limitations should be imposed as are indicated in the appended claims.

We claim:

1. A process for producing a $C_2$ to $C_6$ alcohol which comprises passing a feed stream consisting essentially of water and a $C_2$ to $C_6$ olefin through a hydration reaction zone containing a bed of hydration catalyst comprising an acidic cation exchange resin under hydration reaction conditions producing a $C_2$ to $C_6$ alcohol, wherein olefin is introduced into said reaction zone at multiple points spaced along the length of the catalyst bed, and recovering the alcohol.

2. A process for producing a $C_2$ to $C_6$ alcohol which comprises passing a feed stream consisting of water and a $C_2$ to $C_6$ olefin through a hydration reaction zone containing a bed of hydration catalyst comprising an acidic cation exchange resin under hydration reaction conditions producing a $C_2$ to $C_6$ alcohol, wherein olefin is introduced into said reaction zone at multiple points spaced along the length of the catalyst bed, and recovering the alcohol.

3. The process defined in claim 1 wherein the olefin is propylene.

4. The process defined in claim 1 wherein the acidic cation exchange resin, hydration catalyst is a sulfonated styrene divinylbenzene copolymer.

5. The process defined in claim 1 wherein the water and $C_2$ to $C_6$ olefin are contacted at a mole ratio of from about 5:1 to about 50:1.

6. The process defined in claim 1 wherein the hydration reaction zone contains from about 2 to about 10 olefin injection points.

7. The process defined in claim 1 wherein the alcohol is recovered by counter-current extraction with a solvent at an alcohol to solvent volume ratio of from about 2:1 to about 1:5.

8. The process defined in claim 7 wherein the solvent is a member selected from the group consisting of benzene, a $C_4$ to $C_{12}$ ether and gasoline reformate, and mixtures thereof.

9. The process defined in claim 8 wherein the $C_4$ to $C_{12}$ ether is a member selected from the group consisting of ethyl ether, isopropyl ether, butyl ether, pentyl ether and hexyl ether, and mixtures thereof.

10. The process defined in claim 1 wherein the hydration reaction conditions comprise a temperature of from about 200° F. to about 350° F., a pressure of from about 1,000 p.s.i.g. to about 5,000 p.s.i.g., and a weight hourly space velocity of from about 0.1 to about 10.0 pounds of feed stream per pound of hydration catalyst per hour.

11. The process defined in claim 1 wherein the $C_2$ to $C_6$ olefin is a member selected from the group consisting of ethylene, propylene, butene, pentene, hexene and cyclohexane and mixtures thereof.

12. A process for producing a $C_2$ to $C_6$ alcohol which comprises passing a feed stream consisting essentially of water and a $C_2$ to $C_6$ olefin through a hydration reaction zone containing a bed of hydration catalyst comprising a sulfonated styrene divinylbenzene copolymer at a temperature of from about 255° F. to about 350° F., a pressure of from about 1,200 p.s.i.g. to about 1,500 p.s.i.g., and a liquid hourly space velocity of from about 1 to about 4 pounds of said feed stream per pound of hydration catalyst per hour so as to produce a $C_2$ to $C_6$ alcohol, wherein olefin is introduced into said reaction zone at multiple points spaced along the length of the catalyst bed, and recovering the alcohol.

13. The process defined in claim 12 wherein the $C_2$ to $C_6$ olefin is ethylene, propylene, butene, pentene, hexene, or cyclohexene, or a mixture thereof.

14. The process defined in claim 12 wherein the olefin is propylene.

15. The process defined in claim 12 wherein the water and $C_2$ to $C_6$ olefin are contacted at a mole ratio of from about 10:1 to about 25:1.

16. The process defined in claim 12 wherein the alcohol is recovered by counter-current extraction with a solvent at an alcohol to solvent volume ratio of from about 2:1 to about 1:5.

17. The process defined in claim 16 wherein the solvent is a member selected from the group consisting of benzene, a $C_4$ to $C_{12}$ ether and gasoline reformate, and mixtures thereof.

18. The process defined in claim 17 wherein the $C_4$ to $C_{12}$ ether is a member selected from the group consisting of ethyl ether, isopropanol ether, butyl ether, pentyl ether and hexyl ether, and mixtures thereof.

19. The process defined in claim 12 wherein the feed stream incidentally contains from about 1 to about 15 mole percent of a $C_2$ to $C_6$ paraffin.

20. A process for producing isopropanol which comprises passing a feed stream consisting essentially of water and propylene at a mole ratio of from about 12:1 to about 25:1 through a hydration reaction zone containing a bed of hydration catalyst comprising a sulfonated styrene divinylbenzene copolymer at a temperature of from about 200° F. to about 350° F., a pressure of from about 1,000 p.s.i.g. to about 5,000 p.s.i.g., and a liquid hourly space velocity of from about 0.1 to about 10.0 pounds of water and propylene per pound of catalyst per hour so as to produce isopropanol, wherein propylene is introduced into said reaction zone at multiple points spaced along the length of the catalyst bed, and counter-currently extracting said isopropanol with a solvent selected from the group consisting of gasoline reformate, benzene and isopropyl ether, and mixtures thereof at an isopropanol to solvent volume ratio of from about 2:1 to about 1:5.

21. A process for producing isopropanol which comprises passing a feed stream consisting essentially of water and propylene at a mole ratio of from about 12:1 to about 25:1 through a hydration reaction zone containing a bed of hydration catalyst comprising a sulfonated styrene divinylbenzene copolymer at a temperature of from about 200° F. to about 350° F., a pressure of from about 1,000 p.s.i.g. to about 5,000 p.s.i.g., and a liquid hourly space velocity of from about 0.1 to about 10.0 pounds of water and propylene per pound of catalyst per hour so as to produce isopropanol, wherein propylene is introduced into said reaction zone at multiple points spaced along the length of the catalyst bed, and counter-currently extracting said isopropanol with gasoline reformate at an isopropanol to gasoline reformate volume ratio of from about 2:1 to about 1:5.

22. A process for producing isopropanol which comprises passing a feed stream consisting essentially of water and propylene at a mole ratio of from about 12:1 to about 25:1 through a hydration reaction zone containing a bed of hydration catalyst comprising a sulfonated styrene divinylbenzene copolymer at a temperature of from about 200° F. to about 350° F., a pressure of from about 1,000 p.s.i.g. to about 5,000 p.s.i.g., and a liquid hourly space velocity of from about 0.1 to about 10.0 pounds of water and propylene per pound of catalyst per hour so as to produce isopropanol, wherein propylene is introduced into said reaction zone at multiple ponts spaced along the length of the catalyst bed, and counter-currently extracting said isopropanol with benzene at an isopropanol to benzene volume ratio of from about 2:1 to about 1:5.

23. A process for producing isopropanol which comprises passing a feed stream consisting essentially of water and propylene at a mole ratio of from about 12:1 to about 25:1 through a hydration reaction zone containing a bed of hydration catalyst comprising a sulfonated styrene divinylbenzene copolymer at a temperature of from about 200° F. to about 350° F., a pressure of from about 1,000 p.s.i.g. to about 5,000 p.s.i.g., and a liquid hourly space velocity of from about 0.1 to about 10.0 pounds of water and propylene per pound of catalyst per hour so as to produce isopropanol, wherein propylene is introduced into said reaction zone at multiple points spaced along the length of the catalyst bed, and counter-currently extracting said isopropanol with isopropyl ether, at an isopropanol to isopropyl ether volume ratio of from about 2:1 to about 1:5.

* * * * *